United States Patent [19]

Karami

[11] 3,931,666

[45] Jan. 13, 1976

[54] REUSABLE ADHESIVE DIAPER FASTENER

[75] Inventor: Hamzeh Karami, Crystal Lake, Ill.

[73] Assignee: Colgate-Palmolive Company, New York, N.Y.

[22] Filed: Feb. 4, 1974

[21] Appl. No.: 438,991

[52] U.S. Cl.......... 24/73 VA; 24/DIG. 11; 128/287; 428/40; 428/121; 428/352
[51] Int. Cl.² ...................... A41B 13/02; B32B 3/04
[58] Field of Search ............ 161/99, 102, 109, 110; 117/122 P; 128/156, 284, 287, 290 R; 428/40–43, 55, 54, 77, 121, 124, 131, 132, 198, 202, 343, 352; 24/DIG. 11, 73 VA

[56] References Cited
UNITED STATES PATENTS

| 2,170,147 | 8/1939 | Lane | 206/447 |
|---|---|---|---|
| 2,508,855 | 5/1950 | Brown | 161/73 |
| 2,711,739 | 6/1955 | Fishbein | 117/122 P |
| 3,616,114 | 10/1971 | Hamaguchi et al. | 161/102 X |
| 3,630,201 | 12/1971 | Endres | 128/287 |
| 3,646,937 | 3/1972 | Gellert | 128/287 |
| 3,776,234 | 12/1973 | Hoey | 128/287 |
| 3,794,038 | 2/1974 | Buell | 128/287 |
| 3,810,472 | 5/1974 | Aldinger et al. | 128/287 |

Primary Examiner—George F. Lesmes
Assistant Examiner—Henry F. Epstein

[57] ABSTRACT

A diaper fastener comprising a strip of tape having an adhesive mass disposed over a surface thereof and a unit removably secured to the strip in a longitudinally central portion of the strip. The unit provides an exposed surface (facing away from the strip surface) having a limited affinity for the adhesive. An end portion of the strip is folded over and in contact with the unit exposed surface. The unit itself comprises outer and inner layers of web each of which has a surface which has limited affinity for the adhesive and which faces away from the other layer. The outer layer includes tabs which project longitudinally beyond the ends of the inner layer and which are secured to the strip surface.

6 Claims, 5 Drawing Figures

U.S. Patent  Jan. 13, 1976  3,931,666
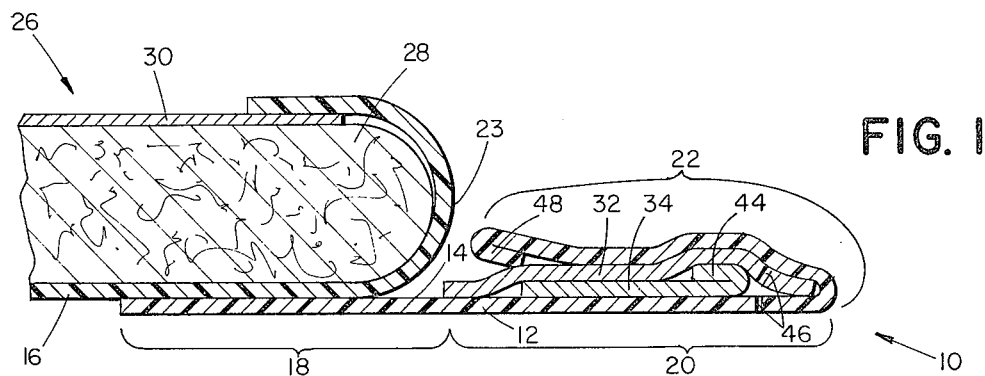
FIG. 1
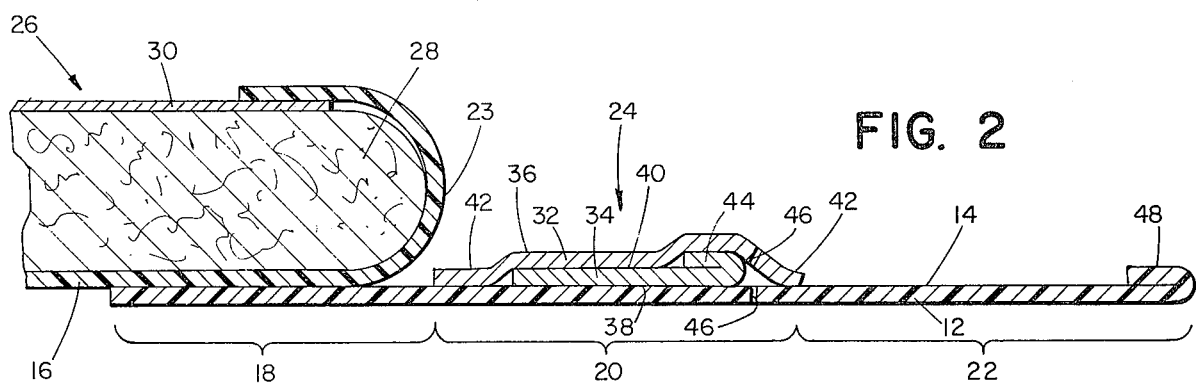
FIG. 2
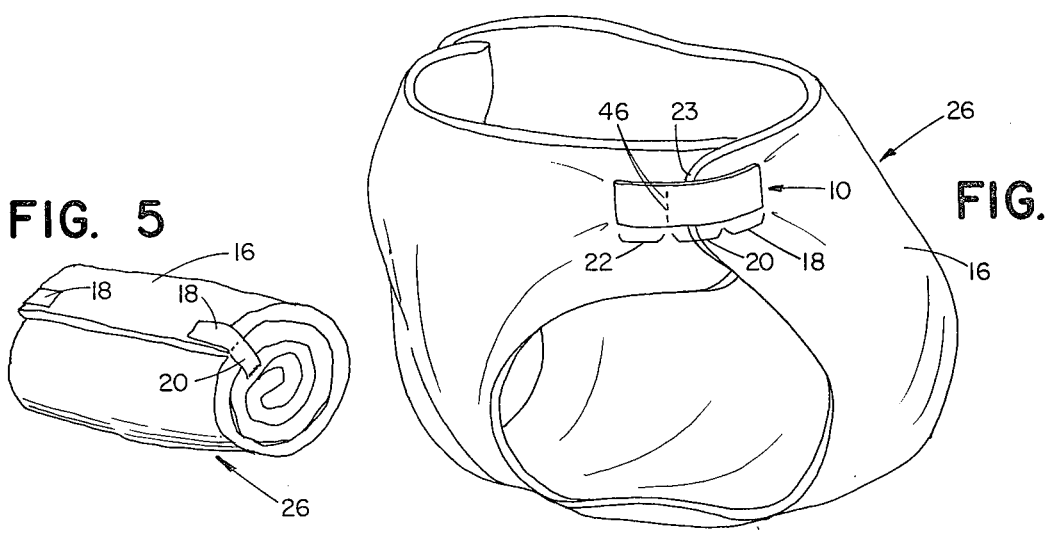
FIG. 5
FIG. 3
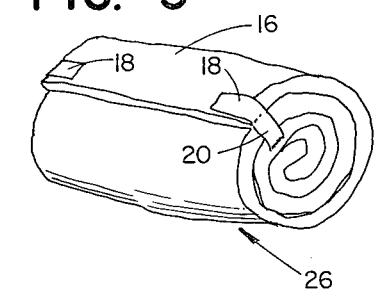
FIG. 4

REUSABLE ADHESIVE DIAPER FASTENER

BACKGROUND OF THE INVENTION

This invention relates to diaper fasteners of the variety which include an adhesive-bearing tape for securing opposite ends of the tape to different parts of the diaper thereby retaining the diaper on an infant.

Tape fasteners of this general variety have been proposed which include a strip of tape and a centrally located release sheet which is adhesively secured to the strip of tape and has an exposed surface which has been treated to have a limited affinity for the adhesive. An end portion of the strip of tape is folded over for contact with that exposed surface thereby retaining the fastener in a folded configuration and protecting the adhesive on that end portion without the necessity of a separate removable release sheet.

SUMMARY OF THE INVENTION

It is a principal object of the present invention to provide for an improved fastener of the type described above. It is an additional object to provide a fastener which, after use, provides an exposed, previously unused region of adhesive mass at a location suitable for securing a soiled diaper in a rolled up configuration with only the exterior water impervious surface exposed.

To achieve these and other objects, a diaper fastener constructed according to the present invention comprises a strip of tape having an adhesive mass disposed over a surface thereof and a unit removably secured to the strip in a longitudinally central portion of the strip. The unit provides the exposed surface, facing away from the strip, which has a limited affinity for the adhesive mass and to which an end portion of the strip of tape is releasably secured. The unit comprises outer and inner layers of web each of which has a surface which has a limited affinity for the adhesive mass and which faces away from the other layer. The outer layer includes tabs projecting longitudinally beyond the ends of the inner layer and secured to the strip surface for retaining the unit to the strip at the desired location. In use, the end portion of the strip may be peeled back from the exposed surface of the unit and then used to secure the diaper to an infant. To remove a soiled diaper, the fastener is torn across its width in its longitudinally central region thereby exposing edges of both the outer and inner layers of the unit. These may be peeled back toward the diaper itself (or completely removed from the remainder of the fastener for separate disposal) to expose the fresh adhesive mass in the longitudinally central portion of the strip of tape. The diaper may then be rolled into a bundle and that fresh adhesive mass employed to retain the diaper in such a bundle, all as further described below.

In preferred embodiments of the invention the strip of tape includes a weakened zone to facilitate such tearing of the fastener for removal of the diaper, the weakened zone is aligned with one of the tabs of the outer layer, and that tab itself also includes a weakened zone.

BRIEF DESCRIPTION OF THE DRAWINGS

Other objects, features, and advantages of the invention will appear from the following description of a particular preferred embodiment taken together with the accompanying drawings in which:

FIG. 1 is a sectional view, through its longitudinal axis, of a fastener constructed according to the present invention and of a portion of the disposable diaper to which it is secured;

FIG. 2 is a view similar to FIG. 1 with a portion of the fastener in an extended position preparatory to application of the diaper to an infant;

FIG. 3 is a perspective view of the diaper fastener retaining a diaper on an infant;

FIG. 4 is a perspective view of a portion of disposable diaper and fasteners constructed according to the present invention after removal of the diaper from the infant; and FIG. 5 is a perspective view of a rolled up soiled diaper retained in its rolled up configuration by fasteners constructed according to the present invention.

DETAILED DESCRIPTION OF A PARTICULAR PREFERRED EMBODIMENT

Referring to FIGS. 1 and 2 diaper fastener 10 comprises a strip of tape 12 having pressure sensitive adhesive disposed on a surface 14 thereof and permanently secured to the conventional plastic, water impervious backing sheet 16 of a disposable diaper by contact of the adhesive on a portion 18 of the strip 12 with the backing sheet 16. The strip of tape 12 also includes a longitudinally central portion 20 and an outer, end portion 22. A unit 24 is disposed on the surface 14 in the central portion 20 of the strip 12. One longitudinal end of the unit is generally aligned with the adjacent lateral margin 23 of the diaper 26, the diaper having the conventional arrangement of an absorbent body 28 disposed between the outer backing sheet 16 and an inner water pervious liner 30.

The unit 24 comprises an outer layer 32 and an inner layer 34 which in the preferred form illustrated consists of separate pieces of paper. The exposed surface 36 of the unit 24 (i.e., the upper surface of outer layer 32) has been treated in a conventional fashion so that it has limited affinity for the adhesive on the surface 14. The lower surface 38 of the inner layer 34 has been similarly treated. Untreated surfaces of the layers are in contact at 40. The outer layer 32 extends longitudinally beyond the ends of the inner layer providing tabs 42 which have their untreated lower surfaces in contact with the adhesive mass on surface 14, thereby firmly securing the layer 32 to the strip 12 and sandwiching the layer 34 therebetween. The layer 34 is provided with an upturned tab 44 which is not secured to the adhesive. The strip 12 and the outer layer 32 are each provided with a weakened zone adjacent the tab 44 of layer 34. These weakened zones may be in the form of aligned lines of perforation 46. The end portion 22 of the strip of tape 12 may be provided with a gripping tab 48 at the end thereof remote from the unit 24.

The operation of the fastener 10 in applying the diaper to an infant proceeds in the same manner as other fasteners of this same general catagory with the parent peeling back the end portion 22 of the strip of tape 12 from the exposed surface 36 of unit 24 to achieve the configuration shown in FIG. 2. The adhesive disposed on surface 14 in the end portion 22 is then available for contact with a remote portion of the diaper after the diaper has been fitted around an infant as shown in FIG. 3.

To remove the diaper the fastener 10 is torn across its width in the central region 20. Lines of perforation 46 facilitate such tearing. The resultant fastener configuration is shown on the left side of FIG. 4 where the severed strip of tape 12 has the layer 34 lightly secured to it over the length of that layer and the layer 32 secured to it firmly but only at an end portion of the layer 32 adjacent the diaper lateral margin 23. The layers 32 and 34 may then be peeled back to overlie the diaper itself (or the layer 34 removed entirely, with the tab 44 facilitating this, as shown in the right side fastener 10 in FIG. 4). With the fasteners in configuration shown at the right side of FIG. 4, the longitudinally central portion 20 of the strip 12 now has fresh adhesive exposed. The diaper may then be rolled up starting at the remote end of the diaper to achieve a configuration such as shown in FIG. 5. The portions 20 are then used to secure the roll against unravelling.

While a particular preferred embodiment of the invention has been illustrated in the accompanying drawings and described in detail herein, other embodiments are within the scope of the invention and the following claims.

I claim:

1. A diaper fastener comprising a strip of tape having a pressure sensitive adhesive disposed over a surface thereof, a unit removably secured to said strip in a longitudinally central portion thereof, said unit providing an exposed surface facing away from said strip surface and having limited affinity for said adhesive, an end portion of said strip folded over and in contact with said exposed unit surface, said unit comprising outer and inner layers of web each of which has a surface which has limited affinity for said adhesive and which faces away from the other layer, said outer layer including tabs projecting longitudinally beyond the ends of the inner layer, said tabs secured to said strip surface, whereby said unit remains in said central strip portion when said end strip portion is removed from said exposed surface of said unit.

2. A diaper fastener as claimed in claim 1 wherein said strip of tape includes a weakened zone to facilitate tearing of the fastener for removal of the diaper.

3. A diaper fastener as claimed in claim 2 wherein said weakened zone is aligned with one of said tabs.

4. A diaper fastener as claimed in claim 3 wherein said one of said tabs also includes a weakened zone.

5. A diaper fastener as claimed in claim 4 wherein said inner layer includes an end portion adjacent said one of said tabs which is unsecured to said strip surface.

6. A diaper fastener as claimed in claim 1 wherein said end portion of said strip includes a gripping tab which is unsecured to said exposed unit surface.

* * * * *